United States Patent
Morita et al.

(10) Patent No.: US 8,065,163 B2
(45) Date of Patent: Nov. 22, 2011

(54) METHODS AND SYSTEMS FOR PROVIDING PATIENT REGISTRATION INFORMATION

(75) Inventors: Mark Morita, Arlington Heights, IL (US); Douglas Gustav Spilling, Elizabethtown, NY (US); Barry Howard Blumenfeld, Needham, MA (US)

(73) Assignee: General Electric Company, Schenectady, NY (US)

( * ) Notice: Subject to any disclaimer, the term of this patent is extended or adjusted under 35 U.S.C. 154(b) by 362 days.

(21) Appl. No.: 11/853,565

(22) Filed: Sep. 11, 2007

(65) Prior Publication Data

US 2009/0070142 A1 Mar. 12, 2009

(51) Int. Cl.
*G06Q 10/00* (2006.01)
*G06Q 50/00* (2006.01)
(52) U.S. Cl. .......................................................... 705/2
(58) Field of Classification Search .................. 705/2, 3, 705/4, 51; 709/217; 395/203; 342/357.13; 340/568.1; 607/60; 455/39
See application file for complete search history.

(56) References Cited

U.S. PATENT DOCUMENTS

| | | | | |
|---|---|---|---|---|
| 5,572,421 A * | 11/1996 | Altman et al. | ..................... | 705/3 |
| 5,737,539 A * | 4/1998 | Edelson et al. | ..................... | 705/3 |
| 6,177,905 B1 * | 1/2001 | Welch | ...................... | 342/357.75 |
| 6,307,471 B1 * | 10/2001 | Xydis | ...................... | 340/568.1 |
| 6,389,461 B1 * | 5/2002 | Shah | ............................. | 709/217 |
| 6,564,104 B2 * | 5/2003 | Nelson et al. | ................... | 607/60 |
| 2003/0114104 A1 * | 6/2003 | Want et al. | ...................... | 455/39 |
| 2004/0103000 A1 * | 5/2004 | Owurowa et al. | ................. | 705/2 |
| 2005/0065815 A1 * | 3/2005 | Mazar et al. | ...................... | 705/2 |
| 2005/0071188 A1 * | 3/2005 | Thuerk | .............. | 705/2 |
| 2006/0085347 A1 * | 4/2006 | Yiachos | ......................... | 705/51 |
| 2006/0173712 A1 * | 8/2006 | Joubert | ............................ | 705/2 |

* cited by examiner

Primary Examiner — Gerald J. O'Connor
Assistant Examiner — John Pauls
(74) Attorney, Agent, or Firm — McAndrews, Held & Malloy, Ltd.; Armando Pastrana, Jr.

(57) ABSTRACT

Certain embodiments of the present invention provide a method of providing patient information. The method includes requesting patient data, supplying the patient data using a mobile electronic device, storing the patient data to a memory associated with the mobile electronic device, and communicating the patient data to a remote data server.

17 Claims, 9 Drawing Sheets

| Name: | Steve Fors |
| Address: | 1313 Mockingbird Lane |
| City: | San Francisco |
| State: | CA |
| Zip: | 90210 |
| Phone: | 800-588-2300 |
| Date of Birth: | 4/1/1957 |
| Insurance: | Guido |
| Employer: | Siemens |
| Med Probs: | Diabetes |
| Allergies: | Peanuts |

Edit    Enter 530    540

FIG. 8

Patient Info Form — Do Not Share

| Name: | Steve Fors | ☐ |
| Address: | 1313 Mockingbird Lane | ☐ |
| City: | San Francisco | ☐ |
| State: | CA | ☐ |
| Zip: | 90210 | ☐ |
| Phone: | 800-588-2300 | ☐ |
| Date of Birth: | 4/1/1957 | ☐ |
| Insurance: | State Life | ☒ |
| Employer: | Siemens | ☐ |

Send

METHODS AND SYSTEMS FOR PROVIDING PATIENT REGISTRATION INFORMATION

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to patient registration. More specifically, the present invention relates to methods and systems for providing patient registration information.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure. Additionally, patients may access information systems for scheduling, diagnosis and/or treatment information, check-in or admission, and/or other tasks. One or more of these systems comprise a healthcare information system, for example.

In typical healthcare settings, the patient registration process is a lengthy and repetitive procedure that patients must endure at nearly every encounter with a healthcare professional. Each new doctor, office, department, or even visit often requires a new set of forms to be completed. Moreover, paper-based forms are still widely-used to document a patient's demographic information, medical history, current medications, allergies, and other information. These paper-based forms are often added to the patient's folder associated with the particular doctor, department, or office being visited. In many settings, the information provided by the patient is transcribed into an electronic healthcare information system. Of course, the transcription process is prone to error in data entry and necessarily results in the patient losing control of his or her data.

In more advanced healthcare enterprises, patients have the ability to input their relevant information directly into an electronic system, thus bypassing the transcription process. For example, kiosk systems enable patients to enter their information at a kiosk that aggregates and transmits the information to the healthcare information system. However, these systems are typically disparate, thus requiring patients to redundantly enter the same information at every new facility or information system they encounter. Moreover, kiosk systems are tied to a physical location, and the ease of access to a kiosk depends on the number of patients waiting to use the kiosk. These systems can also be quite expensive, so smaller healthcare facilities are unlikely to have a multitude of kiosks available for patient use. Additionally, a patient may realize during the registration process that he or she is missing some piece of information required by the system. In such a scenario, the patient may be forced to abandon his or her current registration and vacate the line in order to obtain the necessary information. Furthermore, these systems still may result in a lengthy registration process that cannot be completed, or even begun, until the patient has arrived at the site of the kiosk.

Thus, there is a need for methods and systems that provide one-time input of patient registration information, patient-controlled dissemination of patient data, and secure transferring of patient information that is not tied to a physical location or time. There is a need for methods and systems that provide the remote handshake transfer of patient information during the patient registration process.

BRIEF SUMMARY OF THE INVENTION

Certain embodiments of the present invention provide a method of providing patient information. The method includes requesting patient data, supplying the patient data using a mobile electronic device, storing the patient data to a memory associated with the mobile electronic device, and communicating the patient data to a remote data server. In an embodiment, the processing occurs without the intervention of a user.

Certain embodiments of the present invention provide a system for providing patient information. The system includes a user interface, a memory, a processor, and a communication component. The user interface is adapted to receive patient data. The memory is adapted to store the patient data. The processor is adapted to process the patient data and is associated with a mobile communication device. The communication component is adapted to communicate the patient data to a remote data server.

Certain embodiments of the present invention provide a computer-readable medium including a set of instructions for execution on a computer. The set of instructions includes a request routine configured to request patient data, a supply routine configured to supply the patient data using a mobile communication device, and a communication routine configured to communicate the patient data to a remote data server. In an embodiment, the processing occurs without the intervention of a user.

BRIEF DESCRIPTION OF SEVERAL VIEWS OF THE DRAWINGS

FIGS. 5-9 illustrate exemplary screen shots of an example application of a method of providing patient information used in accordance with an embodiment of the present invention.

Figure 1:
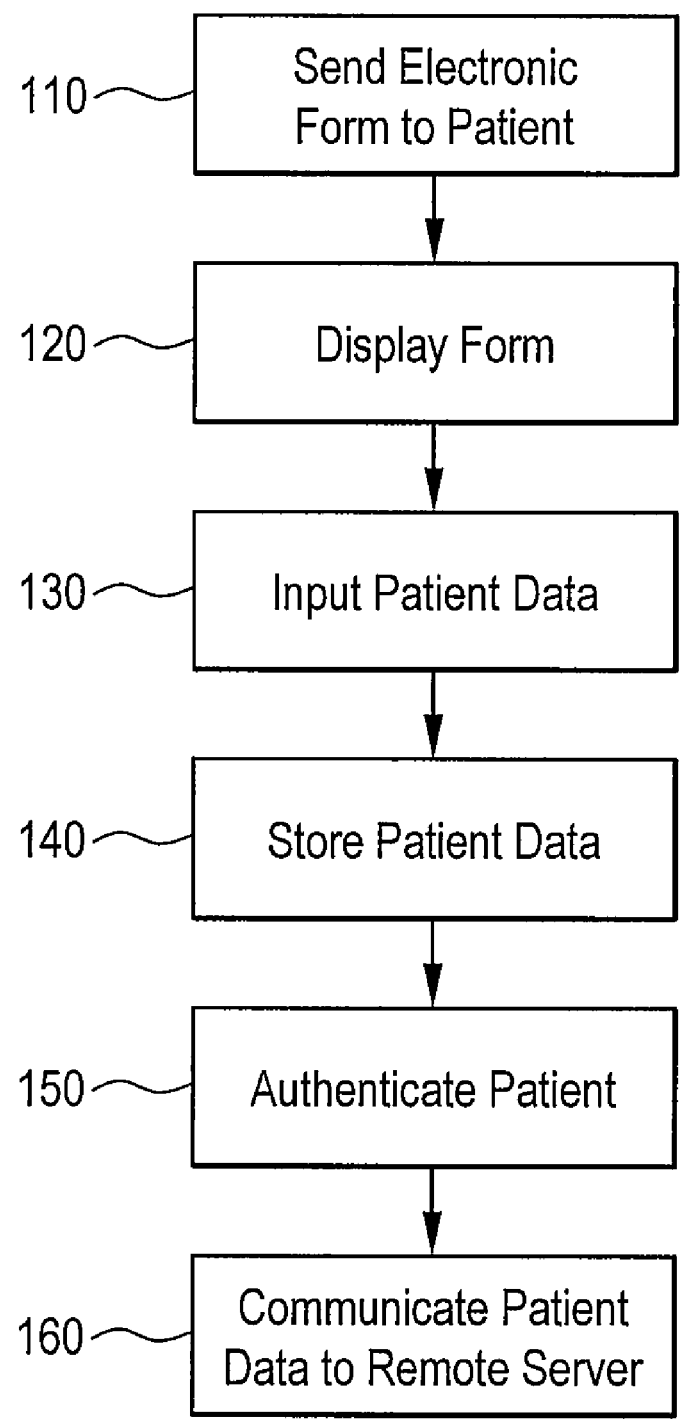
FIG. 1 illustrates a flow diagram for a method of providing new patient information used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a flow diagram for a method 100 for providing new patient information used in accordance with an embodiment of the present invention. The method 100 includes the following steps, which will be described below in more detail. At step 110, an electronic patient information form is sent to the patient. At step 120, the patient information form is displayed for viewing. At step 130, patient data is inputted into the electronic form. At step 140, the patient data is stored to a memory adapted to store electronic data. At step 150, the patient is authenticated. At step 160, the patient data is communicated to a remote server.

At step 110, an electronic patient information form is sent to the patient. In an embodiment, when a patient has an upcoming appointment at a doctor's office, for example, the doctor's office sends an electronic version of a patient information form to the patient prior to the appointment. For example, the patient information form may be sent as an editable portable document format (PDF) document that is attached to an electronic mail message and may be downloaded by the patient.

In other embodiments, the electronic patient information form may be transmitted to the patient in a variety of ways. With regard to format, the patient information form may be sent as a spreadsheet, database entry, or other type of document that may be edited by the patient. In certain embodiments, the patient information form may be accessed by selecting a hyperlink that is associated with an electronic version of the form stored on a server. In an embodiment, this hyperlinked document may be edited directly by the patient, rather than downloaded by the patient and then later edited. Moreover, in another embodiment, the patient information form may be provided in the format of direct questions that are completed sequentially, rather than a comprehensive form. In still another embodiment, the patient information form need not be sent directly to the patient and instead may be sent to the patient's representative, such as a family member or in-home caregiver. Of course, the patient information form may also originate from a source other than a doctor's office. For example, the form may be sent to the patient by a hospital, nurse, or other source of medical care.

At step 120, the patient information form is displayed for viewing. In an embodiment, the patient information form is displayed on a viewing screen associated with, for example, a personal computer or mobile communication device. A mobile communication device may include, for example, a cellular phone, a Pocket PC, a smartphone, or a personal digital assistant (PDA).

At step 130, patient data is inputted into the electronic form. In an embodiment, the patient information form may request, for example, information about the patient's medication history, allergies, past or current medical problems, family medical history, insurance provider, or employer. The patient information form may also request such information as the patient's social security number, contact information, or demographic information. In certain embodiments, the patient information may be inputted into the patient information form using a keyboard or other data input device. In alternative embodiments, the patient information may not be inputted into a specific form that is later provided to a remote server. For example, the patient information may be provided in response to a series of questions provided on a website.

At step 140, the patient data is stored to a memory adapted to store electronic data. In embodiments where the patient information form is downloaded and edited by the patient, the patient data is stored to a memory. For example, the patient data may be stored to a memory associated with the patient's mobile communication device. In this embodiment, the patient information form may be received by the mobile communication device, edited using the device's keypad, and stored to the device's memory. In an embodiment, patient data is stored in data arrays or structures, such that the patient data may be recalled in a variety of configurations. For example, the patient's last name may be stored in a specific data structure so that, when completing future patient information forms, the patient may readily provide his or her last name by recalling the information previously stored in the corresponding data structure.

In an alternative embodiment, the patient data may be stored to a memory associated with a personal computer. For example, a personal computer may receive the patient information form, and the patient may use a keyboard associated with the personal computer to edit the form with the patient's data. The patient data contained in the edited form may then be stored to the personal computer's internal memory. The patient data may then be transferred to an external electronic storage device that may be connected to the personal computer, such as an external hard drive, a universal serial bus (USB) flash drive, a Secure Digital (SD) Card, a Memory Stick (MS), a SmartMedia (SM) device, a Multimedia Card (MMC), a CompactFlash (CF) device, or some other portable memory technology. Alternatively, the patient information form may be stored directly to the electronic storage device, rather than being stored to the internal memory of the personal computer and then transferred to the external electronic storage device.

At step 150, the patient is authenticated. In an embodiment, stored patient data may not be transmitted unless the patient's identity has been authenticated. For example, the patient may be prompted to enter a personal identification number before the patient data may be communicated at step 160.

In alternative embodiments, the patient's identity may be authenticated in a variety of ways. For example, the patient may be authenticated based on a password, a pass phrase, a security token, a security card, a biometric identifier, or some combination thereof. A biometric identifier could include any of a fingerprint, a retinal pattern, an infrared vein pattern, a signature, a voice, a face, a bio-electric signal, or a DNA sequence, for example.

At step 160, the patient data is communicated to a remote server. In an embodiment, the patient data is communicated to a remote server by the patient's mobile communication device. For example, the patient's mobile communication device may communicate the patient data by attaching the edited patient information form to an electronic mail message that is sent over a wireless network to an electronic mail account associated with the doctor's office that originally sent the form. In certain embodiments, some or all of the patient data being communicated is encrypted in order to protect the privacy of the patient.

In alternative embodiments, the patient data may be communicated in a variety of ways. For example, the patient data may be submitted directly to a remote server using an Internet webpage. Additionally, the patient data may be communicated using a personal computer or another electronic device capable of communicating with a server associated with the completed form's destination. In certain embodiments, the patient data may be communicated using a variety of transfer protocols, such as file transfer protocol (FTP), simple mail transfer protocol (SMTP), short message service (SMS) text messaging, or hypertext transfer protocol (HTTP). Moreover, the patient data may be transferred using a multitude of data transfer technologies, such as WiMAX, 3G and 4G cellular systems, Wi-Fi, IEEE 802.11, and Bluetooth, for example.

Figure 2:
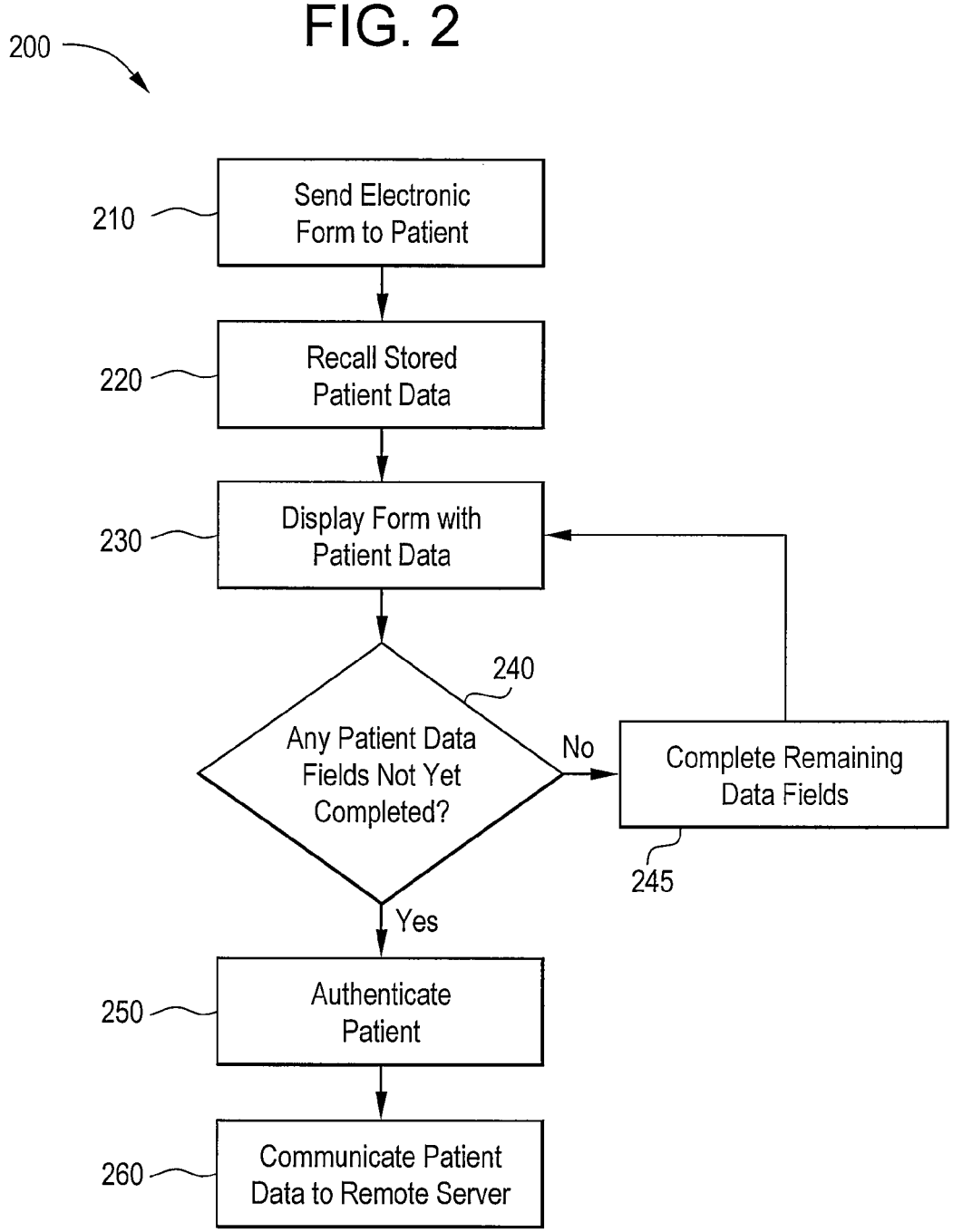
FIG. 2 illustrates a flow diagram for a method of providing patient information used in accordance with an embodiment of the present invention.

FIG. 2 illustrates a flow diagram for a method 200 of providing patient information used in accordance with an embodiment of the present invention. The method 200 includes the following steps, which will be described below in more detail. At step 210, an electronic patient information form is sent to the patient. At step 220, stored patient data is recalled. At step 230, the patient information form is displayed, including the recalled patient data. At decision point 240, it is determined whether any patient data fields still must be completed. If any patient data fields still must be completed, then at conditional step 245, the remaining patient data fields are completed. At step 250, the patient is authenticated. Finally, at step 260, the patient data is communicated to a remote server. In contrast to the method shown in FIG. 1, the method illustrated in FIG. 2 assumes that the patient has already stored at least some patient data in order to complete a previously received patient information form. However, the alternatives described above with regard to FIG. 1 also apply to the steps of the method 200 of providing patient information illustrated in FIG. 2.

At step 210, an electronic patient information form is sent to the patient. In an embodiment, a healthcare provider sends an electronic version of a patient information form to the patient prior to the patient's appointment with the healthcare provider. The alternative embodiments described above with regard to step 110 of FIG. 1 apply to step 210 as well.

At step 220, stored patient data is recalled. In an embodiment, if a patient has previously completed a patient information form, then the patient data used to complete that form may be used to complete future patient information forms. For example, if a patient has previously completed a patient information form that requested the patient's full name, address, and social security number, then that information may be used to complete a new form that requests the patient's full name, address, and social security number. In an embodiment, this data has been previously stored on the patient's personal computer or mobile communication device. To recall the previously stored patient data, the patient may select an "AutoFill" option that, when selected, recalls the previously stored data and populates the corresponding fields in the new patient information form.

In another embodiment, the previously stored patient data may be recalled in a variety of ways. For example, the previously stored data may automatically populate the corresponding fields in the new patient information form without prompting the patient with an "AutoFill" option. Alternatively, the patient may be prompted to populate each field individually with the previously stored patient data corresponding to each field.

At step 230, the patient information form is displayed, including the recalled patient data. In an embodiment, after the previously stored patient data has been recalled, it is displayed on a viewing screen associated with, for example, a personal computer or mobile communication device. In certain embodiments, the patient may be prompted to verify that the previously stored patient data is still accurate. For example, the patient's address may have changed since the patient previously stored his or her address. In an embodiment, the patient may be prompted to correct any inaccurate patient data that has been populated in the new patient information form.

At decision point 240, it is determined whether any patient data fields still must be completed. In an embodiment, the new patient information form is displayed with the previously stored patient data that has been populated in the data fields of the new form. Thus, the patient is able to determine which fields in the new form request patient data that has not been previously stored. In other embodiments, the displayed patient information form may indicate to the patient which fields still must be completed. For example, the fields that still must be completed may be highlighted or displayed in a different color from those that have already been completed.

At conditional step 245, if any patient data fields still must be completed, then the remaining patient data fields are completed. In certain embodiments, the patient information may be inputted into the patient information form using a keyboard or other data input device.

At step 250, the patient is authenticated. In an embodiment, stored patient data may not be transmitted unless the patient's identity has been authenticated based on one or more identifiers. As described above with regard to the authentication step 150 of FIG. 1, the authentication may be based on a personal identification number, a password, a pass phrase, a security token, a security card, a biometric identifier, or some combination thereof.

At step 260, the patient data is communicated to a remote server. In an embodiment, the patient data is communicated to a remote server by the patient's mobile communication device or personal computer. Prior to communicating any patient data to the remote server, the patient may decide to withhold sensitive information. For example, the patient may choose to withhold his or her social security number from the patient data submitted to the remote server. Additionally, some or all of the patient data being communicated may be encrypted in order to protect the privacy of the patient.

Figure 3:
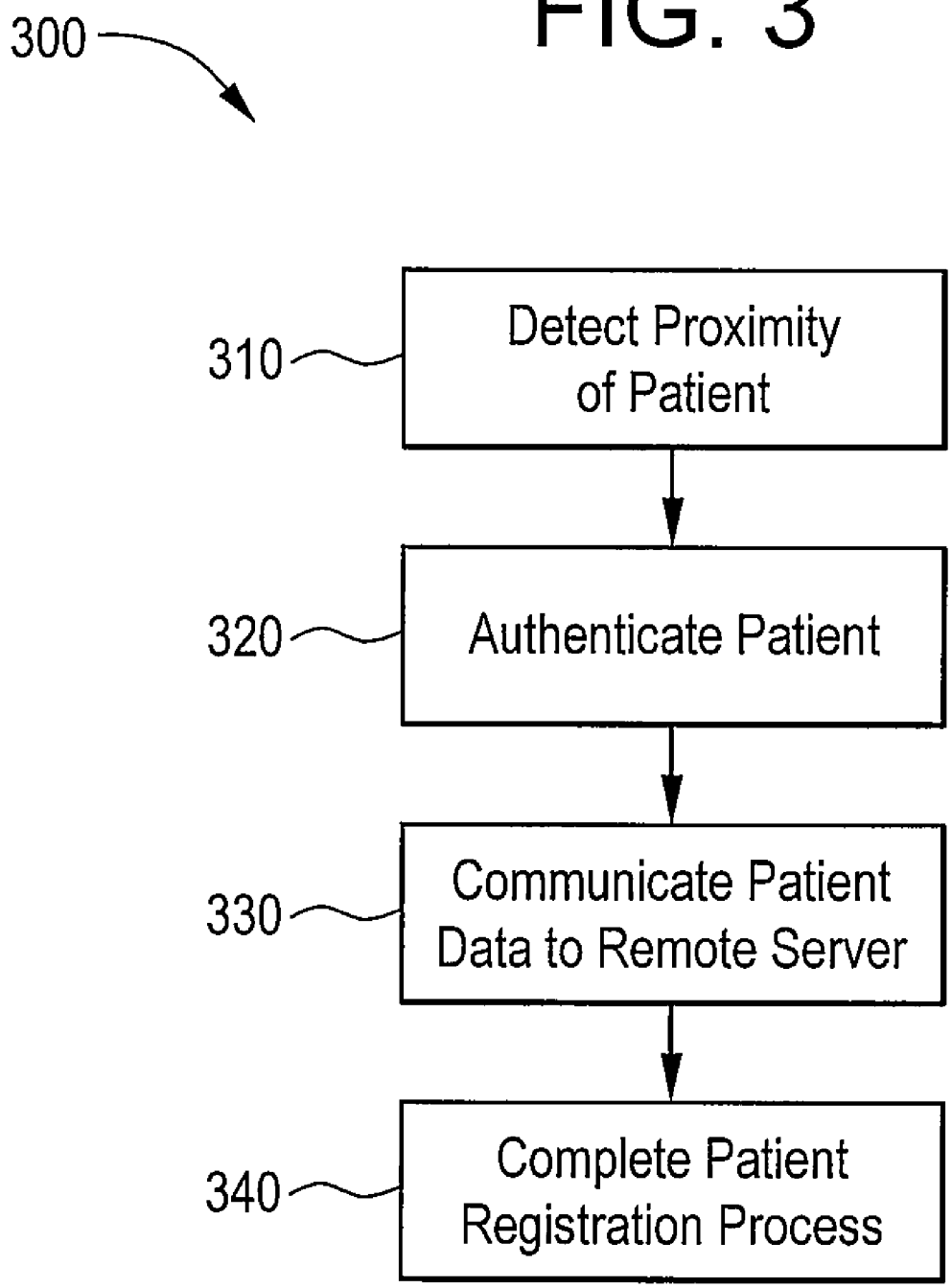
FIG. 3 illustrates a flow diagram for a method for completing patient registration used in accordance with an embodiment of the present invention.

FIG. 3 illustrates a flow diagram for a method 300 for completing patient registration used in accordance with an embodiment of the present invention. The method 300 includes the following steps, which will be described below in more detail. At step 310, the proximity of the patient is detected. At step 320, the patient is authenticated. At step 330, the patient data is communicated to a remote server. At step 340, the patient registration process is completed.

At step 310, the proximity of the patient is detected. In an embodiment, a healthcare information system, such as a HIS, RIS, CIS, or CVIS, for example, detects the proximity of the patient's mobile communication device. For example, if the patient's mobile communication device is configured with an internal global positioning system (GPS) device, then the mobile communication device may communicate its location to the healthcare information system over a wireless network. Once the patient's presence has been detected, the healthcare information system's record for the patient synchronizes with the patient data stored on the mobile communication device. If there is not yet a record for the patient, the mobile communication device may prompt the patient to communicate the patient data stored on the device to the healthcare information system.

In alternative embodiments, the patient's proximity may be detected in numerous ways. For example, the patient's mobile communication device may be detected using radio-frequency identification (RFID), Wi-Fi, Bluetooth, Evolution-Data Optimized (EVDO), Universal Mobile Telecommunications System (UMTS), or infrared technology. In another embodiment, if there is an existing record prior to the patient's arrival, the patient data may not be communicated to the healthcare information system until the patient has approved the transfer. In certain embodiments, the patient may also choose to withhold sensitive information from being transmitted.

At step 320, the patient is authenticated to verify the patient's identity. As described above with regard to FIGS. 1 and 2, certain embodiments contemplate requiring the patient's identity to be authenticated before the patient's data is transferred. As described above with regard to FIGS. 1 and 2, the authentication may be based on a personal identification number, a password, a pass phrase, a security token, a security card, a biometric identifier, or some combination thereof.

At step 330, the patient data is communicated to a remote server. As described above with regard to FIGS. 1 and 2, the patient's data may be communicated to a server associated with the healthcare information system in a variety of ways. Additionally, some or all of the patient data being communicated may be encrypted in order to protect the patient's privacy.

At step 340, the patient registration process is completed. In an embodiment, once the stored patient data has been communicated to the healthcare information system, the patient may be escorted directly to the proper location in the healthcare facility without the need for any further information. Alternatively, if additional information is necessary, such as the patient's signature, then the patient registration process may be completed once the patient provides that additional information. Similarly, if the patient chose to withhold any necessary information during the communication of the stored patient data, such as the patient's social security number, then that information may be provided before the registration process is completed.

The alternative embodiments described above with regard to FIGS. 1 and 2 also apply to the steps of the method 300 for completing patient registration illustrated in FIG. 3.

One or more of the steps of the methods 100, 200, and 300 may be implemented alone or in combination in hardware, firmware, and/or as a set of instructions in software, for example. Certain embodiments may be provided as a set of instructions residing on a computer-readable medium, such as a memory, CD, DVD, or hard disk, for execution on a general purpose computer or other processing device, such as, for example, a PACS workstation.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 4:
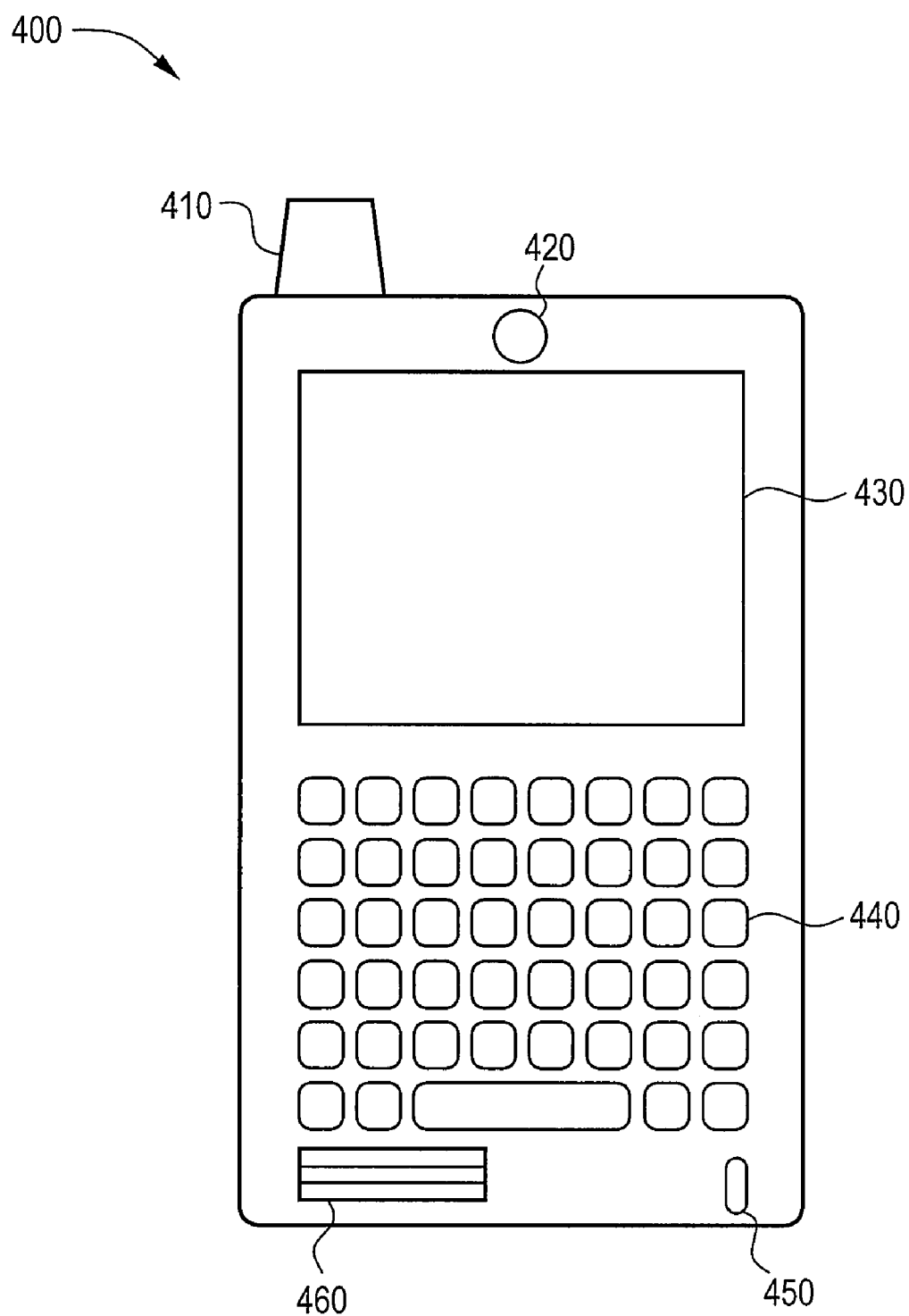
FIG. 4 illustrates a mobile communication device used in accordance with an embodiment of the present invention.

FIG. 4 illustrates a mobile communication device 400 used in accordance with an embodiment of the present invention. The mobile communication device 400 includes an antenna 410, a video camera 420, a display 430, a keypad 440, a microphone 450, and a fingerprint scanner 460. The mobile communication device 400 further includes a processor adapted to process data and a memory adapted to store information electronically.

The antenna 410 is adapted for wireless connectivity to facilitate the transfer of patient data. The video camera 420 is adapted to provide biometric authentication and document scanning. The display 430 provides a user interface for data input and is adapted to display information accessed by or stored on the mobile communication device 400. The keypad 440 provides a user interface for data input. The microphone 450 provides a user interface configured to receive vocal input and is adapted for use in voice authentication. The fingerprint scanner 460 is adapted to scan the fingerprint of a user for identity authentication purposes.

In operation, a patient information form is received by the mobile communication device 400 over a wireless network connection provided by the antenna 410. Once received, the form is stored to a memory associated with the mobile communication device 400. The patient information form is then displayed on the display 430 for viewing by a patient. To accomplish this functionality, the processor associated with the mobile communication device 400 retrieves the stored patient information form from the memory and provides a visual representation of the form to the display 430. The patient may then provide patient data in response to the information requested on the form using one or more of the user interfaces of the mobile communication device 400. For example, the patient may input information manually by using the keypad 440. Alternatively, the patient may provide vocal input using the microphone 450 or visual input using the scanning or video capabilities of the video camera 420. In an embodiment, the video camera 420 is configured with optical character recognition (OCR) capabilities in order to translate scanned documents into editable data.

In an embodiment, once the patient data has been provided, the patient's identity must be authenticated before the patient data may be communicated to the source of the patient information form. For example, the patient may be prompted to provide a fingerprint scan using the fingerprint scanner 460. Alternatively, the video camera 420 may be adapted to provide a facial or retinal scan in order to verify the patient's identify. In still other embodiments, the patient may be prompted to provide a vocal sample using the microphone 450 or a password or pass phrase using the keypad 440.

Upon authentication of the patient's identity, the patient data may be communicated to the patient's healthcare provider over a wireless network using the antenna 410. In addition, the alternatives described above with regard to FIGS. 1-3 also apply to the mobile communication device 400 illustrated in FIG. 4.

In certain embodiments, multiple functions may be performed by a single component of the mobile communication device 400. Alternatively, multiple components of the mobile communication device 400 may work together to perform a single function.

The components and functionality of the mobile communication device 400 may be implemented alone or in combination in hardware, firmware, or as a set of instructions in software, for example. Certain embodiments may be provided as a set of instructions residing on a computer-readable medium, such as a memory, CD, DVD, or hard disk, for execution on a general purpose computer or other processing device, such as a PACS workstation.

FIGS. 5-9 illustrate exemplary screen shots 500, 600, 700, 800, and 900, respectively, of an example application of a method of providing patient information used in accordance with an embodiment of the present invention. In an embodiment, the screen shots 500, 600, 700, 800, and 900 may be associated with a display, which may be similar to the display 430 described above, for example.

The exemplary screen shot 500 includes a plurality of data fields 510, patient data 520, an Edit option 530, and an Enter option 540. The plurality of data fields 510 represent requests that different types of patient data be provided by the patient. For example, one data field 510 requests the patient's ZIP code, while another data field 510 requests the patient's allergies. As shown in FIG. 5, patient data 520 is provided for each of the plurality of data fields 510. For example, "90210" has been provided for the patient's ZIP code, and "Peanuts" has been provided as the patient's allergies. The patient may edit the patient data 520 provided in the plurality of data fields 510 by selecting the Edit option 530. Once the patient is satisfied with the patient data 520 provided, the patient may select the Enter option 540. In certain embodiments, these options may be selected in a variety of ways. For example, if the display is configured with touch-screen capabilities, then an option may be selected manually. Alternatively, an option may be selected using a stylus or other data selector.

Figure 6:
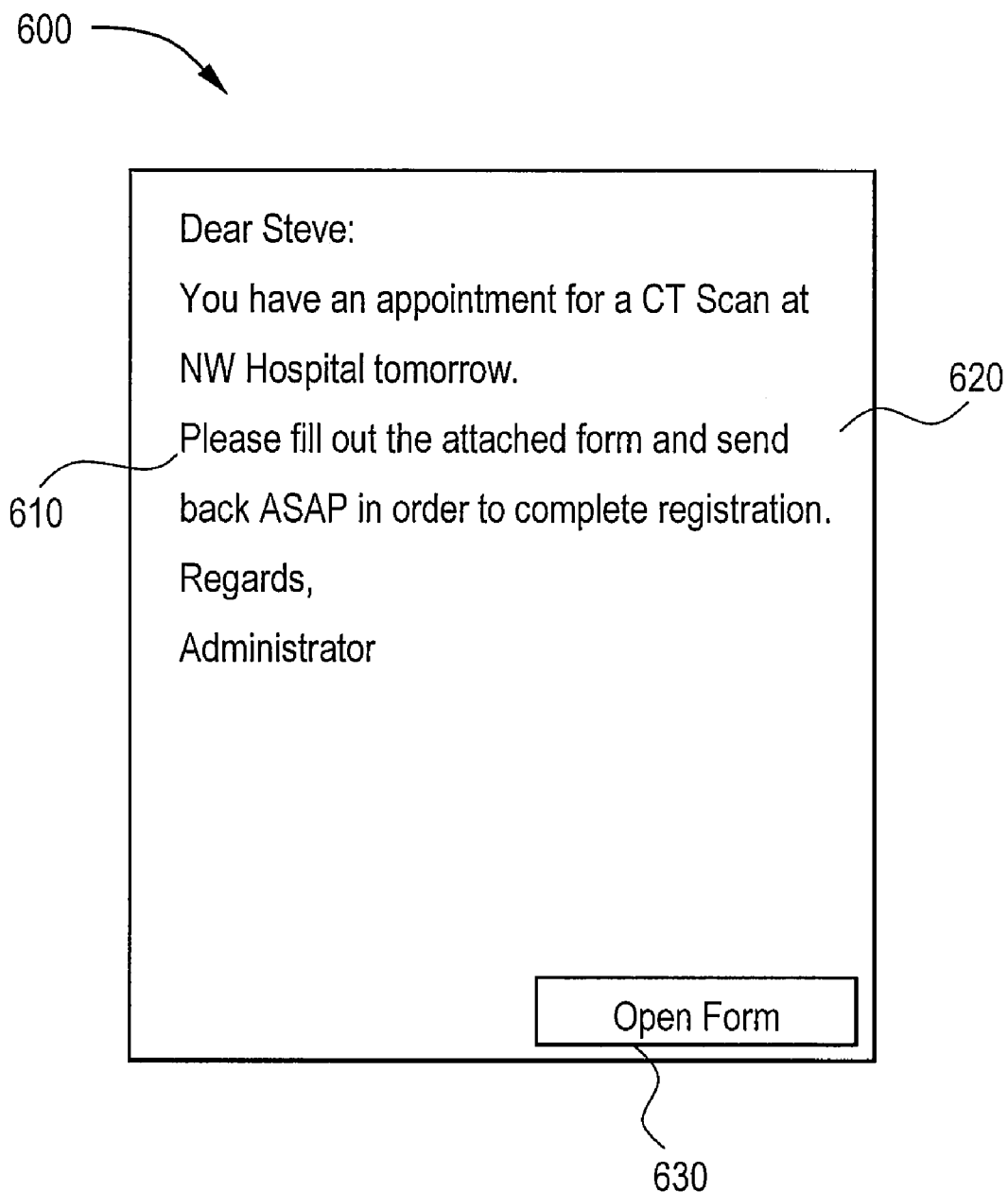

FIG. 6 illustrates an exemplary screen shot 600 that includes an appointment notification 610, a patient data request 620, and an Open Form option 630. To request patient data from a patient, a healthcare provider may send a message to the patient. As shown in FIG. 6, the message may include an appointment notification 610 to remind the patient of an upcoming appointment and a patient data request 620 to request that the patient complete a patient information form prior to the appointment. The message illustrated by screen shot 600 includes an attached patient information form that the patient may access by selecting the Open Form option 630.

Figure 7:

FIG. 7 illustrates an exemplary screen shot 700 of a patient information form that includes a plurality of data fields 710 and an AutoFill option 720. The plurality of data fields 710 represent requests that different types of patient data be provided by the patient. If the patient has previously stored patient data corresponding to the patient data being requested, then that stored patient data may be recalled and used to populate the plurality of data fields 710, as described above with regard to FIG. 2. In certain embodiments, after selecting the AutoFill option 720, the patient may edit the entries that are populated by the previously stored patient data.

FIG. 8 illustrates an exemplary screen shot 800 that includes a plurality of data fields 810, patient data 820, a "Do Not Share" box 830, and a Send option 840. The plurality of data fields 810 represent requests that different types of patient data be provided by the patient. As shown in FIG. 8, patient data 820 has been provided by the patient, either manually or by using an AutoFill function as described above with regard to FIG. 7, for each of the plurality of data fields 810. However, the patient has chosen to withhold some information from the patient data to be sent. In the example shown in FIG. 8, the patient has checked the "Do Not Share" box 830 adjacent to the "Insurance" data field 810. As a result, all patient data 820 shown in the exemplary screen shot 800, besides the patient's insurance information, will be transmitted when the patient selects the Send option 840.

Figure 9:
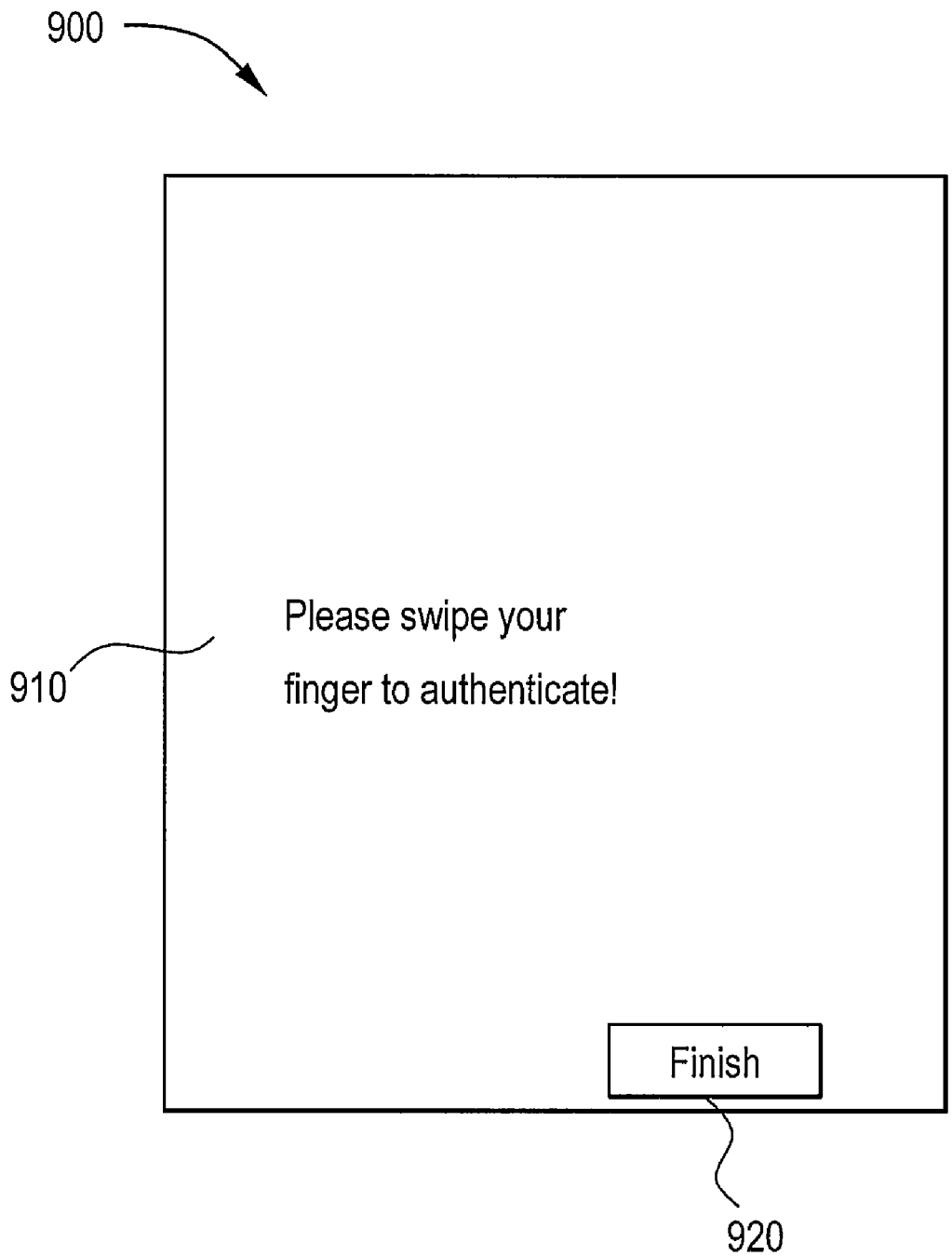

FIG. 9 illustrates an exemplary screen shot 900 that includes an authentication request 910 and a Finish option 920. In an embodiment, a patient is required to provide identity authentication before patient data may be transmitted. Therefore, the patient may be prompted by an authentication request 910 to verify the patient's identity by, for example, providing a fingerprint scan. Once the patient has authenticated, the patient selects the Finish option 920 to indicate that authentication has been provided and that the patient data should be sent once verification of the patient's identity is complete.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method of providing patient information, the method including:
    communicating the geographic location of a mobile communication device to a remote data server;
    receiving a request for patient data from the remote data server at the mobile communication device, said patient data including at least one of a medication history, an allergy, a medical problem, a family medical history, an insurance provider, an employer, a social security number, contact information, and demographic information;
    retrieving patient data from a memory location in the mobile communication device in response to the request;
    displaying the retrieved patient data on the mobile communication device;
    allowing the displayed patient data to be edited using the mobile communication device;
    allowing the displayed patient data to be selected for withholding; and
    communicating from the mobile communication device to the remote server patient data that was not selected for withholding;
    wherein the patient data is communicated from the mobile communication device to the remote server automatically, without user intervention, when the mobile communication device comes within a predetermined location.

2. The method of claim 1, wherein said remote data server is associated with a healthcare information system.

3. The method of claim 1, wherein the request for patient information includes a patient information form comprising at least one patient data field, and wherein displaying patient information on the mobile communication device includes displaying retrieved patient information in the at least one data field of the patient information form on the mobile communication device.

4. The method of claim 1, wherein said patient data is encrypted.

5. The method of claim 1, further including requiring authentication prior to communicating the retrieved patient data to the remote server, wherein said authentication includes a biometric identifier and said biometric identifier includes at least one of a fingerprint, a retinal pattern, an infrared vein pattern, a signature, a voice, a face, a bio-electric signal, and a DNA sequence.

6. The method of claim 1, further including recalling patient data stored on said remote data server.

7. The method of claim 1, wherein said request for patient data comprises a series of questions.

8. The method of claim 1, wherein location of the mobile communication device is detected using a GPS signal.

9. The method of claim 8 wherein the location of the mobile communication device is detected using a GPS signal.

10. The method of claim 1, further including saving patient data edited using the mobile communication device to the memory location on the mobile communication device.

11. A system for providing patient information comprising:

a mobile communication device configured to receive a request for patient data from a remote data server, said patient data including at least one of a medication history, an allergy, a medical problem, a family medical history, an insurance provider, an employer, a social security number, contact information, and demographic information, the mobile communication device including a processor configured to retrieve patient data from a memory location in the mobile communication device in response to the request;

the mobile communication device including a display configured to display the retrieved patient data;

the mobile communication device configured to allow the displayed patient data to be edited using the mobile communication device;

the mobile communication device configured to allow the displayed patient data to be selected for withholding;

the mobile communication device configured to communicate patient data that was not selected for withholding to the remote server; and the mobile communication device configured to communicate the geographic location of the mobile communication device to the remote server;

wherein the mobile communication device is configured to automatically, without user intervention, communicate patient data to the remote server when the mobile communication device comes within a predetermined location.

12. The system of claim 11, wherein the request for patient information includes a patient information form comprising at least one patient data field, and wherein the mobile communication device is configured to display the retrieved patient information in the at least one data field of the patient information form on the mobile communication device.

13. The system of claim 11, wherein the mobile communication device is configured to require authentication prior to communicating the retrieved patient data to the remote server.

14. The system of claim 11, wherein the mobile communication device is configured to recall patient data stored on the remote data server.

15. The system of claim 11, wherein the mobile communication device is configured to allow the patient data edited using the mobile communication device to be saved to the memory location on the mobile communication device.

16. The system of claim 11, wherein the mobile communication device is configured to transmit the location of the mobile communication device to the remote server using a GPS signal.

17. A non-transitory computer readable medium including a set of instructions for execution on a computer, the set of instructions including:

a first routine configured to receive a request for patient data from a remote data server at a mobile communication device, said patient data including at least one of a medication history, an allergy, a medical problem, a family medical history, an insurance provider, an employer, a social security number, contact information, and demographic information;

a second routine configured to retrieve patient data from a memory location in the mobile communication device in response to the request;

a third routine configured to display the retrieved patient data on the mobile communication device;

a fourth routine configured to allow the displayed patient data to be edited using the mobile communication device;

a fifth routine configured to allow the displayed patient data to be selected for withholding;

a sixth routine configured to communicate the geographic location of the mobile communication relative to the remote server; and a seventh routine configured to automatically, without user intervention, communicate patient data that was not selected for withholding from the mobile communication device to the remote server when the mobile communication device comes within a predetermined location.

* * * * *